US008017793B2

(12) United States Patent
Hida et al.

(10) Patent No.: US 8,017,793 B2
(45) Date of Patent: Sep. 13, 2011

(54) OXIDATION OF ALCOHOL WITH USE OF HYDROGEN PEROXIDE AND TUNGSTEN CATALYST

(75) Inventors: Takemasa Hida, Hyogo (JP); Kyozo Kawata, Osaka (JP); Mikio Kabaki, Hyogo (JP)

(73) Assignee: Shionogi & Co., Ltd., Osaka (JP)

( * ) Notice: Subject to any disclaimer, the term of this patent is extended or adjusted under 35 U.S.C. 154(b) by 683 days.

(21) Appl. No.: 11/596,280

(22) PCT Filed: May 12, 2005

(86) PCT No.: PCT/JP2005/008666
§ 371 (c)(1),
(2), (4) Date: Jun. 13, 2008

(87) PCT Pub. No.: WO2005/110958
PCT Pub. Date: Nov. 24, 2005

(65) Prior Publication Data
US 2008/0269509 A1    Oct. 30, 2008

(30) Foreign Application Priority Data
May 14, 2004    (JP) .................................. 2004-144754

(51) Int. Cl.
*C07C 27/10*    (2006.01)
*C07C 69/00*    (2006.01)
*C07D 307/77*    (2006.01)
(52) U.S. Cl. ...................... 549/297; 560/129; 568/700
(58) Field of Classification Search .................. 549/297; 560/129; 568/700
See application file for complete search history.

(56) References Cited

U.S. PATENT DOCUMENTS

| 4,613,704 | A | 9/1986 | Papenfuhs |
| 4,754,073 | A | 6/1988 | Venturello et al. |
| 5,248,807 | A | 9/1993 | Fujimoto et al. |
| 5,463,107 | A | 10/1995 | Konoike et al. |
| 2005/0215817 | A1 | 9/2005 | Sato et al. |

FOREIGN PATENT DOCUMENTS

| EP | 1 489 091 A1 | 12/2004 |
| GB | 2 199 325 A | 7/1988 |
| JP | 60-132952 | 7/1985 |
| JP | 62-228037 | 10/1987 |
| JP | 63-190898 | 8/1988 |
| JP | 07-053484 | 2/1995 |
| JP | 7-316188 | 12/1995 |
| JP | 09-118687 | 5/1997 |
| JP | 2002-241631 | 8/2002 |
| JP | 2003-171333 | * 6/2003 |
| WO | WO 92/12991 | 8/1992 |
| WO | WO 94/21583 | 9/1994 |
| WO | WO 03/080643 A1 | 10/2003 |
| WO | WO 2004/011412 A1 | 2/2004 |

OTHER PUBLICATIONS

Christian Reichardt, Solvents and Solvent Effects in Organic Chemistry, 2003, Wilety-Vch Verlag GmbH & Co., 3rd ed., p. 471-507.*
K. Sato et al., "Organic Solvent- and Halide-Free Oxidation of Alcohols with Aqueous Hydrogen Peroxide", J. Am. Chem. Soc., 119, pp. 12386-12387 (1997).
T. Konoike et al., "Practical Partial Synthesis of Myriceric Acid A, an Endothelin Receptor Antagonist, from Oleanolic Acid", J. Org. Chem., 62, pp. 960-966 (1997).
K. Sato, et al., "A Practical Method for Alcohol Oxidation with Aqueous Hydrogen Peroxide under Organic Solvent- and Halide-Free Conditions", Bulletin of Chemical Society of Japan, 1999, vol. 72, p. 2287-2306.
S.E. Jacobson, et al., "Oxidation of Alcohols by Molybdenum and Tungsten Peroxo Complexes", Journal of Organic Chemistry, 1979, vol. 44, p. 921-924.
O. Bortolini et al., "Metal Catalysis in Oxidation by Peroxides. Molybdenum- and Tungsten-Catalyzed Oxidations of Alcohols by Diluted Hydrogen Peroxide under Phase-Transfer Conditions," Journal of Organic Chemistry, 1986, vol. 51, p. 2661-2663.
K. Sato, et al., "A Halide-Free Method for Olefin Epoxidation with 30% Hydrogen Peroxide," Bulletin of Chemical Society of Japan, 1997, vol. 70, p. 905-915.
K. Sato, et al., "A "Green" Route to Adipic Acid: Direct Oxidation of Cydohexenes with 30 Percent Hydrogen Peroxide", Science, 1998, vol. 281, p. 1646-1647.
K. Sato, et al., "Oxidation of sulfides to sulfoxides and sulfones with 30% hydrogen peroxide under organic solvent- and halogen-free consitions," Tetrahedron, 2001, vol. 57, p. 2469-2476.
C. Venturello, et al., "A New, Effective Catalytic System for Epoxidation of Olefins by Hydrogen Peroxide under Phase-Transfer Conditions", Journal of Organic Chemistry, 1983, vol. 48, p. 3831-3833.
T. Konoike et al., "Practical Large-Scale Synthesis of Endothelin Receptor Antagonist S-0139", Organic Process Research and Development, 1999, vol. 3, p. 347-351.
T. Konoike, et al., "Practical Partial Synthesis of Myriceric Acid A, an Endothelin Receptor Antagonist, from Oleanolic Acid", Journal of Organic Chemistry, 1997, vol. 62, p. 960-966.
Y. Usui, et al., "A green method of adipic acid synthesis: organic solvent- and halide-free oxidation of cycloalkanones with 30% hydrogen peroxide", Green Chemistry, 2003, vol. 5, p. 373.
English translation of a part of JP 2002-241631 (original document submitted in an IDS filed on Nov. 13, 2006), 12 pages.
English translation of JP 09-118687 (original document submitted in an IDS filed on Nov. 13, 2006), 29 pages.
English language translation of International Preliminary Report on Patentability issued in PCT/JP2005/008666, Nov. 23, 2006, 5 pages.

* cited by examiner

*Primary Examiner* — Taylor Victor Oh
(74) *Attorney, Agent, or Firm* — Finnegan, Henderson, Farabow, Garrett & Dunner LLP

(57) ABSTRACT

Disclosed is a method for oxidizing an alcohol in an amide solvent using a mixed reagent containing hydrogen peroxide and a tungsten catalyst.

12 Claims, No Drawings

OXIDATION OF ALCOHOL WITH USE OF HYDROGEN PEROXIDE AND TUNGSTEN CATALYST

TECHNICAL FIELD

The present invention relates to oxidation of alcohols with use of hydrogen peroxide and a tungsten catalyst. In particular, the present invention relates to a process of producing a ketooleanolic acid that can be an intermediate for synthesis of pharmaceuticals.

BACKGROUND ART

In recent years, in the industrial production processes of chemical substances, reactions that minimize the environmental pollution is regarded as being important. Oxidation of alcohols is one of the important chemical reactions, so that the development of reaction that has a high applicability and that does not give adverse effects to the environment is desired.

Non-patent document 1 discloses oxidation of alcohols with use of hydrogen peroxide solution and a tungsten catalyst. However, in order to allow the reaction to proceed smoothly, a condition with a pH value of 3 or below is required, and it is disclosed that the reaction wherein pH value is 3.2 gives a yield of 57%, and the reaction wherein pH value is 4.4 lowers gives the yield to be 27%. Also, according to the process disclosed in the document, the reaction is carried out with no solvent or with use of toluene as a solvent. Therefore, it has been difficult to apply the reaction disclosed in the document to the oxidation of compounds that are unstable to acid or compounds that are insoluble to toluene.

Non-patent document 2 discloses oxidation of an alcohol with use of hydrogen peroxide solution and peroxotungstate; however, it uses 90% hydrogen peroxide solution, so that it is unsuitable for mass synthesis because of the danger of explosion. It does not refer to use of any amide solvent or the pH value in the reaction conditions.

Non-patent document 3 discloses oxidation of alcohols with use of hydrogen peroxide solution and sodium tungstate. However, it discloses that, when a tungsten catalyst is used, a pH value of 1.4 is preferable and, when the acidity lowers, the selectivity of reaction decreases considerably. Since a halogenated carbon solvent is used, it is not preferable also in view of the environment. It has a problem such as using 70% hydrogen peroxide solution that is highly dangerous.

Patent document 1 discloses a process of producing carboxylic acid by oxidizing an oily solution of alicyclic alcohol or an oily solution of alicyclic ketone in a non-homogeneous solution system with use of hydrogen peroxide solution and tungstic acid. However, this document also fails to refer to use of an amide solvent and the pH value in the reaction condition.

Non-patent documents 4 to 7 and 10 disclose a process of epoxidation of olefin, a process of producing adipic acid from cyclohexane, cyclohexanol, or cyclohexanone, a process of producing sulfoxide or a sulfone compound from sulfide, a process of producing methylsulfinyl compound from a methylthio compound, or the like with use of hydrogen peroxide solution and a tungsten catalyst.

Patent documents 2 to 4 disclose oxidation with use of hydrogen peroxide and tungstate under a neutral or basic condition. Patent documents 4 and 5 disclose that N,N-dimethylacetamide can be used in the oxidation with use of hydrogen peroxide solution and tungstate. However, none of these disclose oxidation of alcohols.

Ketooleanolic acid represented by the formula (II):

[Chemical Formula 1]

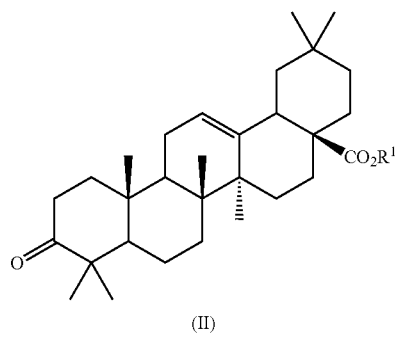

(II)

(wherein $R^1$ is hydrogen or lower alkyl)
(hereafter referred to as compound (II)) is a compound that can be an intermediate of a compound represented by the formula (A):

[Chemical Formula 1]

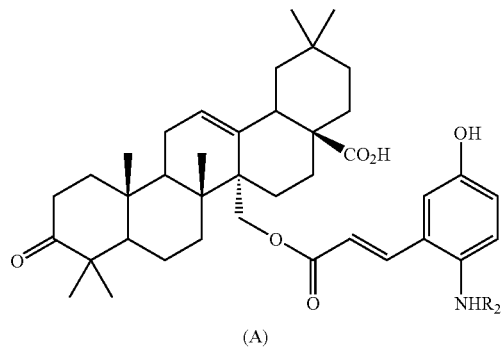

(A)

(wherein $R^2$ is hydrogen or —$R^3$-$R^4$; $R^3$ is —$SO_3$—, —$CH_2COO$—, —$COCOO$—, or —$COR^5COO$— wherein $R^5$ represents alkylene having a carbon number of 1 to 6 or alkenylene having a carbon number of 2 to 6; and $R^4$ represents hydrogen or alkyl having a carbon number of 1 to 6) (hereafter referred to as compound A), or a pharmaceutically acceptable salt thereof.

The compound A is known to be useful as a drug for treating various circulatory organ diseases (for example, high blood pressure, ischemic diseases, cerebral circulation disorders, renal disorders, circulation failure of various organs, asthma, stroke, brain infarction, brain edema, and others) (See patent documents 6 and 7), and the synthesis process of compound A is disclosed in patent documents 8, 9, non-patent documents 8 and 9, and others.

Patent document 8 and non-patent document 9 disclose a process of oxidizing oleanolic acid in chloroform-acetone or dichloromethane-acetone solvent with use of a Jones reagent; however, it necessitates use of an environmentally harmful reagent such as chromic acid, chloroform, dichloromethane or the like, so that it has not necessarily been a satisfactory process as an industrial production process.

Patent document 1 International Patent Publication WO2004/011412 Pamphlet
Patent document 2 Japanese Patent Application Laid-Open (JP-A) No. 60-132952 Gazette
Patent document 3 Japanese Patent Application Laid-Open (JP-A) No. 63-190898 Gazette Patent document 4 Japanese Patent Application Laid-Open (JP-A) No. 2002-241631 Gazette
Patent document 5 Japanese Patent Application Laid-Open (JP-A) No. 09-118687 Gazette
Patent document 6 International Patent Publication WO92/12991 Pamphlet
Patent document 7 Japanese Patent Application Laid-Open (JP-A) No. 07-53484 Gazette
Patent document 8 Japanese Patent Application Laid-Open (JP-A) No. 07-316188 Gazette
Patent document 9 International Patent Publication WO2003/80643 Pamphlet
Non-patent document 1 Bulletin of Chemical Society of Japan, 1999, Vol. 72, p. 2287-2306
Non-patent document 2 Journal of Organic Chemistry, 1979, Vol. 44, p. 921-924
Non-patent document 3 Journal of Organic Chemistry, 1986, Vol. 51, p. 2661-2663
Non-patent document 4 Bulletin of Chemical Society of Japan, 1997, Vol. 70, p. 905-915
Non-patent document 5 Science, 1998, Vol. 281, p. 1646-1647
Non-patent document 6 Tetrahedron, 2001, Vol. 57, p.
Non-patent document 7 Journal of Organic Chemistry, 1983, Vol. 48, p. 3831-3833
Non-patent document 8 Organic Process Research And Development, 1999, Vol. 3, p. 347-351
Non-patent document 9 Journal of Organic Chemistry, 1997, Vol. 62, p. 960-966
Non-patent document 10 Green Chemistry, 2003, Vol. 5, p. 373

DISCLOSURE OF THE INVENTION

Problems that the Invention is to Solve

Development of an oxidation process of an alcohol being safe, having a high applicability, and being applicable to industrial production has been desired.

Means for Solving the Problems

The present invention provides:
(1) A process of oxidizing alcohol characterized by reacting an alcohol with use of hydrogen peroxide and a tungsten catalyst in an amide solvent;
(2) A process of oxidizing alcohol characterized by reacting an alcohol with use of a mixed reagent containing hydrogen peroxide and a tungsten catalyst in an amide solvent;
(3) The process of (2), wherein the mixed reagent further contains phosphoric acid, a salt or a hydrate thereof;
(4) The process of (2) or (3), wherein the pH value of the mixed reagent or the pH value in the reaction system before the start of reaction is 2 or above;
(5) The process of any one of (2) to (4), wherein the pH value of the mixed reagent or the pH value in the reaction system before the start of reaction is 5 or above;
(6) The process of any one of (2) to (5), wherein the pH value of the mixed reagent or the pH value in the reaction system before the start of reaction is 8 or below;
(7) The process of (1) characterized by allowing an alcohol to react in the presence of phosphoric acid, a salt or a hydrate thereof;
(8) The process of any one of (1) to (7), wherein the tungsten catalyst is tungstic acid, sodium tungstate or a hydrate thereof;
(9) The process of any one of (1) to (8), wherein the amide solvent is N,N-dimethylacetamide;
(10) The process of any one of (3) to (9), wherein the phosphoric acid, a salt or a hydrate thereof is disodium phosphate, monosodium phosphate or a hydrate thereof, or a mixture thereof;
(11) A process of producing a compound represented by the formula (II):

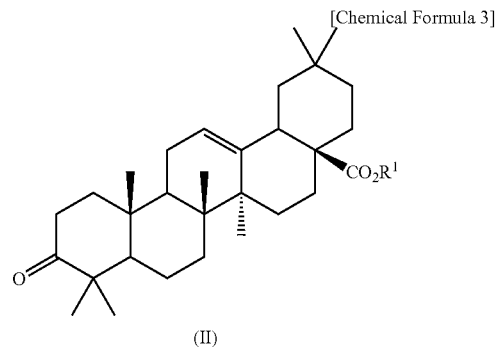

[Chemical Formula 3]

(II)

(wherein $R^1$ is hydrogen or lower alkyl)
characterized by oxidizing a compound represented by the formula (I):

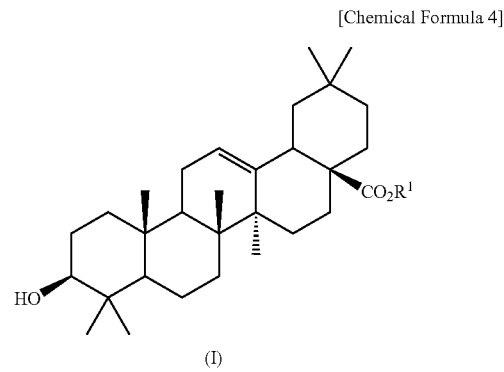

[Chemical Formula 4]

(I)

(wherein $R^1$ is hydrogen or lower alkyl)
(hereafter referred to as compound (I)) with use of hydrogen peroxide and a tungsten catalyst in an amide solvent; and
(12) A process of producing a compound represented by the formula (III):

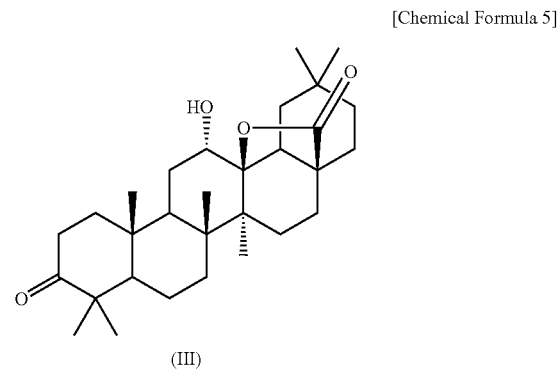

[Chemical Formula 5]

(III)

(hereafter referred to as compound (III))
characterized in that the compound (II) obtained by the process of (11) is successively subjected to ozone oxidation without isolation;

(13) A process of producing a compound represented by the formula:

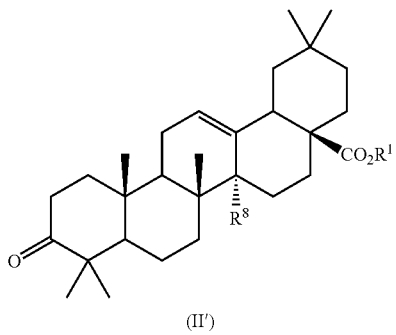

[Chemical Formula 6]

(II')

(wherein R$^1$ is hydrogen or lower alkyl, and R$^8$ has the same meaning as R$^7$ described below or a group obtained by substitution of the group)
characterized by oxidizing a compound represented by the formula:

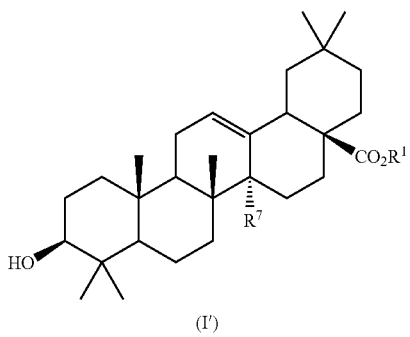

[Chemical Formula 7]

(I')

(wherein R$^1$ is hydrogen or lower alkyl, and R$^7$ is lower alkyl optionally having a substituent) with use of hydrogen peroxide and a tungsten catalyst in an amide solvent;
(14) A process of producing a compound represented by the formula (III) of (12), characterized in that the compound represented by the formula (II') which is obtained by the process of (13) is successively subjected to ozone oxidation without isolation.

Effects of the Invention

According to the process of the present invention, oxidation of various alcohols can be allowed to proceed efficiently under an acidic to weakly basic condition.

BEST MODES FOR CARRYING OUT THE INVENTION

In the present invention, "alcohol" include primary alcohols and secondary alcohols.
The reaction included in the "oxidation process of alcohol" in the present invention includes a process of obtaining ketone from a secondary alcohol, a process of obtaining carboxylic acid from a primary alcohol, and a process of obtaining aldehyde from a primary alcohol.

The primary alcohol may be, for example, myricerone, saturated aliphatic primary alcohol (ethanol, 1-propanol, 1-butanol, 1-pentanol, 1-hexanol, 1-heptanol, 1-octanol, 1-nonanol, 1-decanol, or the like), benzyl alcohol, 2-phenylethanol, or the like.

The secondary alcohol may be, for example, oleanolic acid, saturated aliphatic secondary alcohol (2-propanol, 2-butanol, 2-pentanol, 3-pentanol, 2-hexanol, 3-hexanol, 2-heptanol, 3-heptanol, 4-heptanol, 2-octanol, 3-octanol, 4-octanol, 2-nonanol, 3-nonanol, 4-nonanol, 5-nonanol, 2-decanol, 3-decanol, 4-decanol, 5-decanol, 2-ethyl-1,3-hexanediol, or the like), alicyclic alcohol (cyclohexanol, cycloheptanol, cyclooctanol, cyclononanol, or the like), 1-phenylethanol, 1-phenylpropanol, or the like.

When a substrate is to be subjected to oxidation according to the process of the present invention, the reaction can be allowed to proceed by successively adding hydrogen peroxide and a tungsten catalyst to a solution containing a solvent and the substrate; however, the reaction can be allowed to proceed conveniently if hydrogen peroxide and a tungsten catalyst are mixed in advance to prepare a mixed reagent.

As hydrogen peroxide, hydrogen peroxide solution may be used, and the concentration thereof is not particularly limited as long as it is of a degree that is typically used. The concentration is preferably 5 to 60 wt %, more preferably 8 to 35 wt % and more preferably 30 to 35 wt %.

The upper limit of the amount of use of hydrogen peroxide is not particularly limited. The amount of use of hydrogen peroxide is typically 0.1 mol equivalent to 10 mol equivalent, preferably 0.1 mol equivalent to 5 mol equivalent, more preferably 0.5 mol equivalent to 3 mol equivalent and more preferably 1 mol equivalent to 2 mol equivalent, with respect to one mole of the substrate.

The tungsten catalyst is not particularly limited as long as it is one that is generally used. Examples of the tungsten catalyst include tungstic acid, sodium tungstate, potassium tungstate, calcium tungstate, cobalt (II) tungstate, lead (II) tungstate, barium tungstate, magnesium tungstate, lithium tungstate, ammonium tungstate, ammonium metatungstate, ammonium paratungstate, phosphotungstic acid, silicotungstic acid, and hydrates thereof. Particularly, tungstic acid or sodium tungstate, or a hydrate thereof is preferable.

The amount of use of the tungsten catalyst is 0.001 mol equivalent to 0.3 mol equivalent, preferably 0.005 mol equivalent to 0.1 mol equivalent, more preferably 0.01 mol equivalent to 0.05 mol equivalent, as tungsten with respect to one mole of the substrate.

In the process of the present invention, the reaction can be allowed to proceed further suitably by carrying out the reaction in the presence of phosphoric acid or a salt thereof, or a hydrate thereof. The phosphoric acid or a salt thereof, or a hydrate thereof can be added either directly into the reaction system or to the above-mentioned mixed reagent.

Examples of the phosphate include, for example, ammonium dihydrogenphosphate, potassium dihydrogenphosphate, sodium dihydrogenphosphate (monosodium phosphate), calcium dihydrogenphosphate, disodium dihydrogenpyrophosphate, sodium metaphosphate, potassium metaphosphate, sodium hexametaphosphate, sodium metaphosphate, diammonium hydrogenphosphate, dipotassium hydrogenphosphate, disodium hydrogenphosphate (disodium phosphate), sodium polyphosphate, potassium polyphosphate, sodium tripolyphosphate, sodium tetrapolyphosphate, sodium pentapolyphosphate, potassium pyrophosphate, sodium pyrophosphate, tripotassium phosphate, trisodium phosphate, hydrate thereof, and a mixture of two or more kinds of them. Preferably, it is a buffer consisting of disodium phosphate dodecahydrate, monosodium phosphate dihydrate and water, an aqueous solution of phosphoric acid, an aqueous solution of disodium phosphate, disodium phosphate dodecahydrate, trisodium phosphate dodecahydrate, potassium dihydrogenphosphate or dipotassium hydrogenphosphate.

These may be added as a phosphate, or alternatively an aqueous solution or a phosphate buffer may be prepared in advance and this may be added at the time of preparing a mixed reagent.

The amount of the phosphoric acid or a salt thereof, or a hydrate thereof to be added into the reaction system or the mixed reagent differs depending on the concentration of hydrogen peroxide solution, the kind of the catalyst and phosphate, the pH value of the mixed reagent, and the like. For example, it may be added in an amount of about 0.5 to 5 mol equivalent, preferably 0.7 to 4.5 mol equivalent, relative to one equivalent of the tungsten catalyst.

The pH value of the mixed reagent prepared in advance is not particularly limited; however, it is preferable that the pH value is within a range from 1 to 9. When the pH value is out of this range, the oxidation does not proceed suitably, thereby giving adverse effects such as slowing of the reaction speed, decrease in the object compound yield, increase of the byproducts, and the like. Therefore, applicability as an industrial production process will be low.

The lower limit of the pH value of the mixed reagent is preferably 2.5, more preferably 3, still more preferably 5, further still more preferably 6, and most preferably 6.5.

The upper limit of the pH value of the mixed reagent is preferably 8.5, more preferably 8, and most preferably 7.5.

The mixed reagent prepared in the above manner is added to an alcohol dissolved in an amide solvent and they are mixed. The "pH value in the reaction system before the start of reaction" in the present invention refers to the pH value at this time point. A preferable pH range in the reaction system before the start of reaction is similar to the pH value of the above-described mixed reagent.

A mixture of the mixed reagent, the amide solvent, and the alcohol is allowed to react at about 40° C. to 150° C. for 10 minutes to 24 hours, preferably one hour to four hours, to obtain an oxidized object compound.

Examples of the amide solvent include 1,3-dimethyl-2-imidazolidinone, N,N-dimethylformamide, 1-methyl-2-pyrrolidone, N,N-dimethylacetamide, triamide hexamethylphosphate, and the like. Particularly, N,N-dimethylacetamide or 1-methyl-2-pyrrolidinone is preferable.

The amount of the solvent is not particularly limited; however, about 1 ml to 10 ml, preferably 2 ml to 4 ml, may be used relative to one millimol equivalent of the substrate.

After the reaction is completed, extraction of the product with a hydrophobic solvent such as toluene, reduction of excessive hydrogen peroxide with a reducing agent such as L-ascorbic acid, and a salting-out operation with brine may be carried out by an ordinary method, if needed.

As one preferable mode of the oxidation of obtaining carboxylic acid or aldehyde from a primary alcohol, the oxidation of myricerone which is a known compound may be raised.

[Chemical Formula 8]

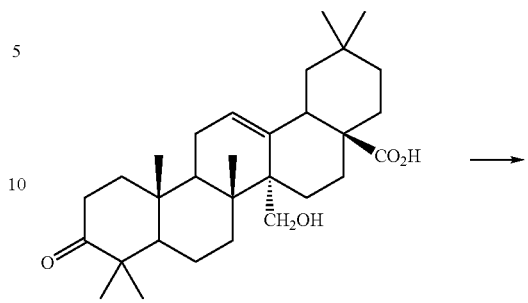

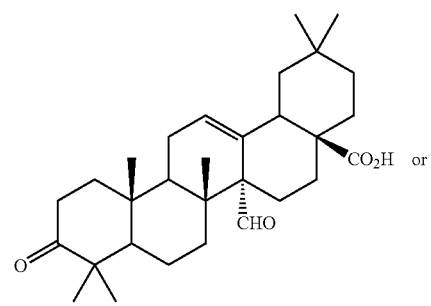

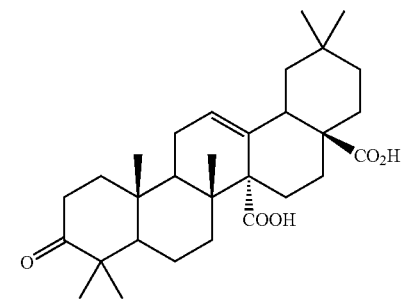

As one mode of the reaction of obtaining ketone from a secondary alcohol, the process of obtaining the compound (II) from the above compound (I) may be raised.

[Chemical Formula 9]

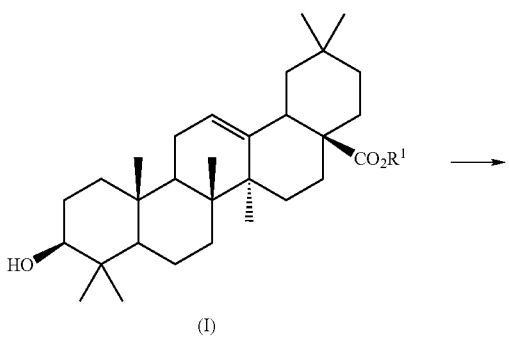

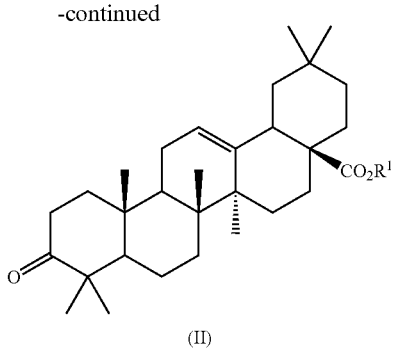

(II)

(wherein R¹ is hydrogen or lower alkyl) Also, as another mode, the oxidation of myricerol which is a known compound may be raised.

[Chemical Formula 10]

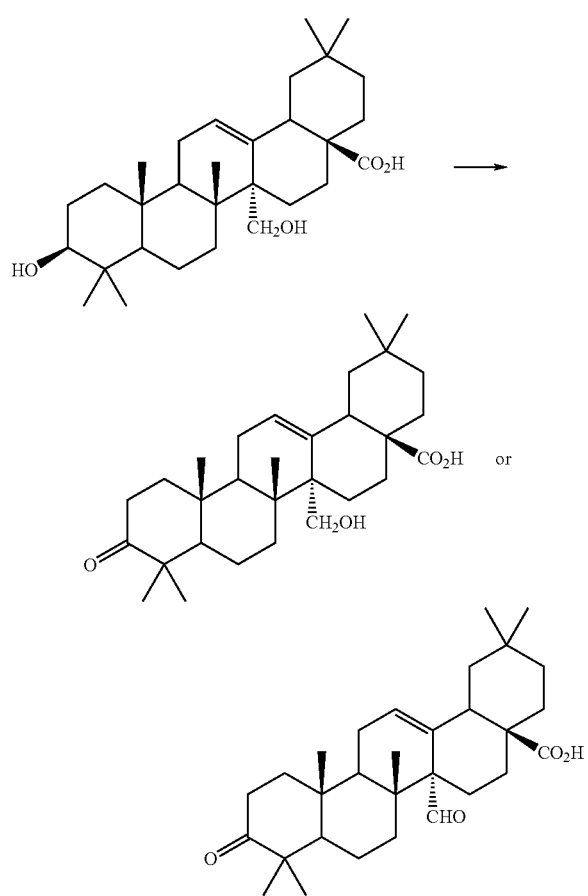

In the present specification, lower alkyl includes straight-chain and branched-chain alkyls having a carbon number of 1 to 8, and examples thereof include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, and the like. Methyl is preferable.

"Lower alkyl optionally having a substituent" is not particularly limited as long as it is lower alkyl substituted with a group that cannot be a hindrance to the process of the present invention. Examples of the substituent include halogen, optionally protected hydroxy, lower alkoxy, carboxy, lower alkoxycarbonyl, arylcarbonyl, acyl, acyloxy, aryl, aryloxy, amino, lower alkylamino, acylamino, and the like. Lower alkyl substituted with hydroxy is preferable and hydroxymethyl is especially preferable. "Halogen" includes fluorine, chlorine, bromine, and iodine.

Examples of the protective group of "optionally protected hydroxy" include aryl lower alkyl such as triphenylmethyl and benzyl, lower alkoxy(lower)alkyl such as methoxymethyl, 1-ethoxyethyl, 1-methyl-1-methoxyethyl and the like, lower alkoxy(lower)alkoxy (lower)alkyl such as methoxyethoxymethyl and the like, lower alkylthio(lower)alkyl such as methylthiomethyl and the like, tetrahydropyranyl, tetrahydrothiopyranyl, tetrahydrofuranyl, tetrahydrothiofuranyl, aryl(lower)alkyloxy(lower)alkyl such as benzyloxymethyl and the like, lower alkylsulfonyl, p-toluenesulfonyl, and the like.

The lower alkyl moiety of "lower alkoxy", "lower alkoxycarbonyl", "lower alkylamino", "aryl(lower)alkyl", "lower alkoxy(lower)alkyl", "lower alkoxy(lower)alkoxy(lower) alkyl", "lower alkylthio(lower)alkyl", "aryl (lower)alkyloxy (lower)alkyl", and "lower alkylsulfonyl" is similar to the above-described "lower alkyl".

"Acyl" includes straight-chain or branched chain-form aliphatic acyl having a carbon number of 1 to 6, preferably a carbon number of 1 to 4, cyclic aliphatic acyl having a carbon number of 4 to 9, preferably a carbon number of 4 to 7, and aroyl. Specifically, "acyl" includes formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl, and the like.

The acyl moiety of "acyloxy" and "acylamino" is similar to the above-described "acyl".

"Aryl" includes phenyl, naphthyl, anthryl, phenanthryl, indenyl, and the like. The aryl moiety of the "arylcarbonyl", "aryloxy", "aryl(lower)alkyl" and "aryl(lower)alkyloxy(lower)alkyl" is also similar.

The "group obtained by oxidation of the group" in $R^8$ includes formyl or carboxy, for example, when $R^7$ is hydroxymethyl, and includes formyl or alkyl having a carbon number of n−1 and substituted with carboxy when $R^7$ is alkyl having a carbon number of n (n is 2 or more) and substituted with hydroxy.

Oxidations of the compound (I) were carried out with use of a mixed reagent (pH 1) made of hydrogen peroxide solution and a tungsten catalyst or a mixed reagent (pH 7) obtained by further adding phosphate to this. It was found out that, in the latter, the production of byproducts is restrained, and the amount of addition of hydrogen peroxide can be restrained to the stoichiometrical amount with respect to the substrate. Therefore, in the process of obtaining the compound (II) from the compound (I), it is preferable to add phosphoric acid or a salt thereof, or a hydrate thereof into the reaction system or into the mixed reagent in advance.

When dimethylsulfoxide, hypochlorite, or 2,2,6,6-tetramethyl-1-piperidinyloxy radical (TEMPO) is used as an oxidizing reagent to be used for oxidation of the compound (I), or when ammonium molybdate is used as a catalyst, undesired results have been obtained such as progression of by-reaction or stoppage of the reaction. Therefore, in the process of obtaining the compound (II) from the compound (I), use of hydrogen peroxide and a tungsten catalyst is one characteristic feature of the present invention.

The compound (II) obtained by the process of the present invention is subjected to a subsequent step after isolation by an ordinary method or without isolation, thereby to obtain the compound (III).

[Chemical Formula 11]

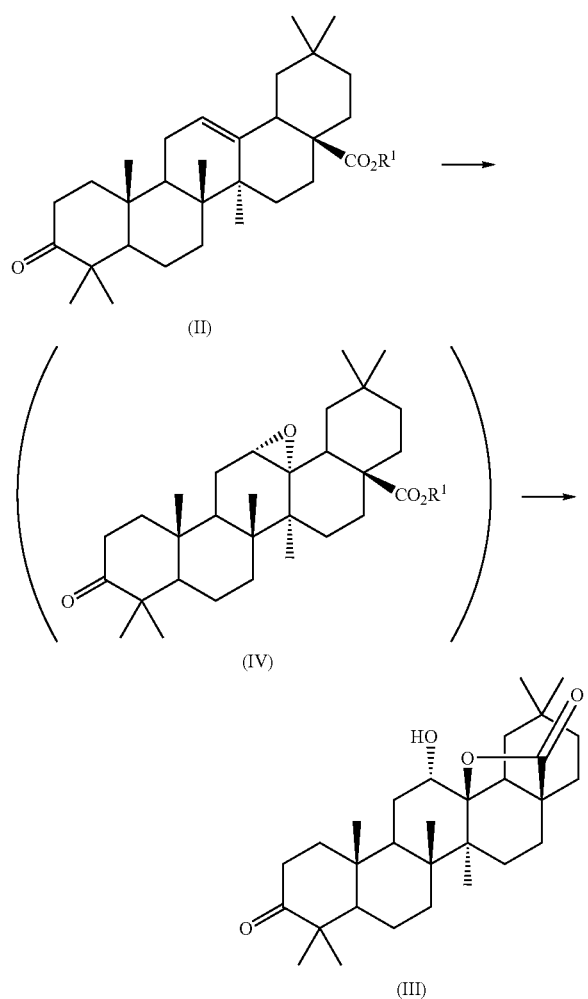

For example, the solvent is concentrated for the time being, if needed, from the solution (organic layer) containing the compound (II) obtained by the above-described process; a suitable solvent and an alcohol (preferably methanol) are added; and the compound (II) is oxidized with use of ozone gas. Specifically, ozone gas is introduced at −60° C. to 0° C., preferably −50° C. to −20° C., and the reaction is allowed to take place for 10 minutes to 24 hours, preferably 30 minutes to 5 hours.

After the reaction is completed, a reducing agent such as L-ascorbic acid and a solvent are added, if needed, and a suitable acid is added at 10° C. to 50° C., preferably 30° C. to 40° C. for crystallization of the compound (III). Subsequently, alcohol (preferably methanol) is added, the mixture is stirred for about 10 minutes to one hour, and filtration may be carried out to obtain a purified compound (III).

The solvent is not particularly limited as long as it is one that is generally used. The same solvent as used in the previous step may be preferably used.

The compound (III) can be obtained directly from the compound (II), however, a compound (IV) may be obtained from the compound (II) and, after it is isolated by an ordinary process, the compound (III) may be obtained.

The compound (III) can be isolated by an ordinary process, however, in the case of using the compound as an intermediate for synthesis of the compound A, the object compound can be produced by the process disclosed in the patent document 7, the patent document 8, or the like without isolation.

The process of the present invention has the following advantages, and is extremely useful as an industrial production process.

Halogenated hydrocarbon such as dichloromethane or harmful solvents or reagents such as chromic acid and manganese dioxide are not used.

Tungsten catalysts have no toxicity or little toxicity.

The amount of discarded phosphorus can be reduced because the reaction proceeds with a catalyst amount of the tungsten catalyst, and the amount of use of phosphoric acid depends on the amount of use of the tungsten catalyst.

Hydrogen peroxide solution of 5 to 40 wt % has a low danger of explosion.

The non-patent document 1 discloses that the pH value of 3 or less is preferable; however, according to the present process, the reaction proceeds suitably even under a neutral condition. Therefore, the process has an advantage in that it can be used for the oxidation of a substrate that is unstable to acid.

Also, the non-patent document 1 discloses reaction using no solvent or using toluene. It is difficult to apply a non-solvent reaction to oxidation of a solid substance. The solvent used in the process of the present invention, particularly N,N-dimethylacetamide, can be applied also to a slightly soluble substance, so that the present process is a reaction having a high applicability.

Hereafter, Examples and Experimental Examples will be shown; however, these do not limit the scope of the present invention. In the Examples, the abbreviations each have the following meaning.

DME: ethylene glycol dimethyl ether
DMI: 1,3-dimethyl-2-imidazolidinone
DMF: N,N-dimethylformamide
NMP: 1-methyl-2-pyrrolidone
DMA: N,N-dimethylacetamide
HMPA: triamide hexamethylphosphate Example 1

[Chemical Formula 12]

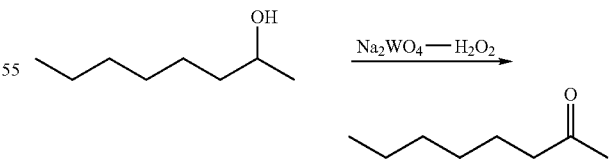

Into 30% hydrogen peroxide solution (1.05 g, 9.3 mmol), 25.3 mg of sodium tungstate dihydrate (0.077 mol) was dissolved to prepare a mixed reagent (pH 5.4). The mixed reagent and 1.0 g of 2-octanol (7.7 mmol) were mixed with 18 mL of each of the following solvents, and the mixture was heated to 90° C. The reaction was continued for 3 hours to obtain an object compound.

The results are shown below.

TABLE 1

| | Solvent | Reaction temperature (°C.) | 2-octanone yield (%)[1] |
|---|---|---|---|
| Examples | DMI | 90 | 40 |
| | DMF | 90 | 50 |
| | NMP | 90 | 73 |
| | DMA | 90 | 74 |
| | HMPA | 90 | 88 |
| Comparative Examples | diglyme | 90 | 0 |
| | DME | 85 | 0 |
| | dioxane | 90 | 0 |
| | ethanol | 78 | 1 |
| | acetonitrile | 80 | 7 |
| | acetone | 54 | 0 |

[1] calculated by GC quantification

From the above results, it will be understood that the oxidation proceeds suitably when an amide solvent is used.

Example 2

[Chemical Formula 13]

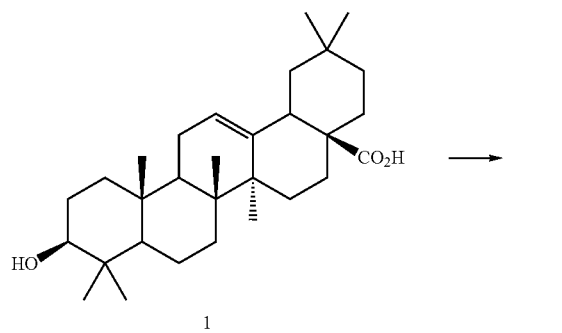

1

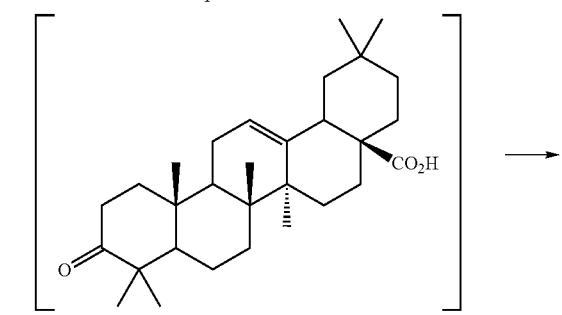

2

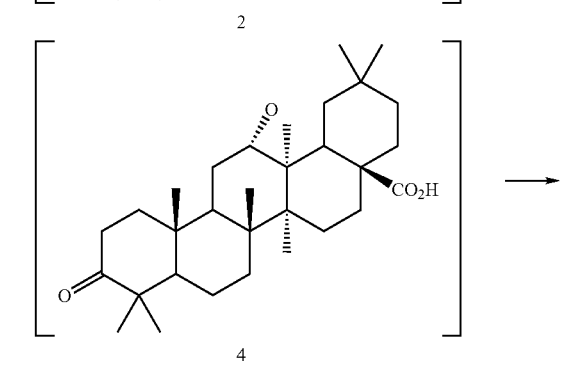

4

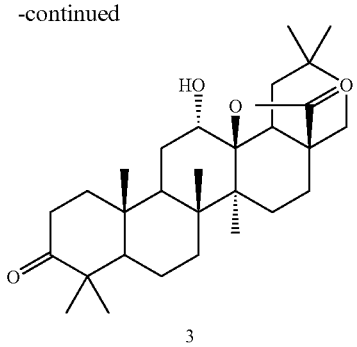

3

After 400 mg of sodium tungstate dihydrate (1.21 mmol) was dissolved into 2.9 g of 35% hydrogen peroxide solution (29.9 mmol), a phosphate buffer (170 mg of disodium phosphate dodecahydrate (0.47 mmol), 80 mg of monosodium phosphate dihydrate (0.51 mmol), 9.5 g of water) was added to prepare a mixed reagent (pH 7.1). The compound 1 (11.0 g, 24.1 mmol) was dissolved into 57 mL of DMA, and the mixture was heated to 90° C. Then, the above mixed Reagent was dropwise added over about one hour. After the dropwise addition was completed, the reaction was continued at 90° C. for 30 minutes, and the resultant was cooled to 45° C. After 55 mL of toluene was allowed to flow into the resultant, 55 mL of 5% brine containing 0.85 g of L-ascorbic acid was allowed to flow into the resultant and stirred while maintaining the temperature at 40° C. or above. After an organic layer was separated at 40° C. or above, the resultant was concentrated to 17 g under reduced pressure, and 84 mL of DMA and 18 mL of methanol were allowed to flow into the resultant. Thereafter, the resultant was cooled to −40° C., and ozone gas was introduced. After the reaction was completed, a DMA solution (10.5 g) containing 2.2 g of L-ascorbic acid was allowed to flow into the resultant, and the temperature was raised up to 30° C., followed by addition of 62% sulfuric acid (1.9 g) for crystallization. Then, 22 mL of methanol was allowed to flow into the resultant and the mixture was stirred for 30 minutes. The reacted mixture was filtrated to obtain the compound 3 as a white crystal. The yield was 8.6 g (76%).

Compound 4: $^1$H-NMR (500 MHz, CDCl$_3$), δ0.816 (s, 3H), 0.883 (s, 3H), 0.945 (s, 3H), 0.977 (s, 3H), 0.992 (s, 3H), 1.068 (s, 3H), 1.139 (s, 3H), 1.22 (m, 1H), 1.25 (m, 1H), 1.33 (m, 1H), 1.33 (m, 1H), 1.36 (m, 1H), 1.39 (m, 1H), 1.40 (m, 1H), 1.43 (m, 1H), 1.45 (m, 1H), 1.47 (m, 1H), 1.49 (m, 1H), 1.65 (m, 1H), 1.67 (m, 1H), 1.69 (m, 2H), 1.906 (ddd, J=13.3, 7.2, 5.1 Hz, 1H), 1.78 (m, 2H), 1.98 (m, 1H), 2.00 (m, 1H), 2.01 (m, 1H), 2.444 (ddd, J=16.2, 8.7, 7.2 Hz, 1H), 2.465 (ddd, J=16.2, 8.3, 5.1 Hz, 1H), 3.197 (t, J=1.8 Hz, 1H)

$^{13}$C-NMR (500 MHz, CDCl$_3$) δ 16.80, 19.26, 21.252, 22.41, 22.59, 23.30, 24.21, 27.30, 29.21, 30.35, 32.62, 33.16, 33.20, 33.95, 34.00, 36.18, 37.92, 39.21, 40.28, 40.50, 42.74, 47.00, 47.58, 54.37, 63.64, 67.02, 183.15, 218.34

Example 3

Into 1.18 g of 35% hydrogen peroxide solution (12.0 mmol), 144 mg of disodium phosphate dodecahydrate (0.4 mmol) and 33 mg of sodium tungstate dihydrate (0.1 mmol) were dissolved to prepare a mixed reagent (pH 6.5). After 4.58 g of the compound 1 (10.0 mmol) was dissolved into 23 mL of N,N-dimethylacetamide, the resultant was heated to 90° C., and the above mixed reagent was added. After the reaction was continued at 90° C. for four hours, 50 mL of toluene and 50 g of 5% brine were added for liquid separation. After the organic layer was separated, the resultant was concentrated under reduced pressure, and acetonitrile solution (25 mL of acetonitrile, 5 mL of water) was added to obtain the compound 2 as a white crystal. The yield was 4.12 g (90%).

Example 4

Into 0.38 g of 34.5% hydrogen peroxide (3.86 mmol), 0.16 mmol of tungstic acid or sodium tungstate dihydrate was dissolved, and 1.35 g of arbitrary 0.1 mol/L phosphate buffer was added to prepare a mixed reagent. After 1.5 g of oleanolic acid (3.28 mmol) was dissolved into 15.6 mL of N,N-dimethylacetamide, the resultant was heated to 90(C. The above mixed reagent was added, and the reaction was continued for 90 minutes while maintaining the temperature of 90(C to obtain the compound 2. The yield ratio was calculated by HPLC quantification.

TABLE 2

| Catalyst | Mixed reagent pH | Yield (%) | Phosphate buffer |
| --- | --- | --- | --- |
| $H_2WO_4$ | 1.92 | 96.36 | aqueous solution of phosphoric acid |
|  | 2.73 | 96.61 | aqueous solution of disodium phosphate |
| $Na_2WO_4$ | 5.40 | 96.84 | aqueous solution of phosphoric acid |
|  | 7.14 | 97.86 | phosphate buffer (pH 6.77)* |
|  | 8.06 | 98.14 | aqueous solution of disodium phosphate |

*phosphate buffer (0.34 g of disodium phosphate dodecahydrate, 0.15 g of monosodium phosphate dihydrate, 18.9 ml of water)

Example 5

Into 30% hydrogen peroxide solution (1.05 g, 9.36 mmol), 25 mg of sodium tungstate dihydrate (0.076 mmol) and 121 mg of disodium phosphate dodecahydrate (0.34 mmol) were dissolved to prepare a mixed reagent. The above mixed reagent and 1.0 g of 2-octanol were mixed with 18 mL of DMA, and the mixture was heated to 90° C. The reaction was continued for 3 hours to obtain an object compound. Also, experiments were carried out in a similar manner with use of a mixed reagent to which phosphoric acid has been added and a mixed reagent to which no phosphoric acid has been added. The results are shown below.

TABLE 3

| Mixed reagent pH | Additive[1] | 2-octanone yield (%)[2] |
| --- | --- | --- |
| 1.0 | $H_3PO_4$ | 92 |
| 5.4 | — | 74 |
| 6.5 | $Na_2HPO_4 \cdot 12H_2O$ | 94 |

[1] 4 mol equivalent/tungsten catalyst
[2] calculated by GC quantification

Example 6

Into 5.90 g of 35% hydrogen peroxide solution (60.0 mmol), 720 mg of disodium phosphate dodecahydrate (2.0 mmol) and 165 mg of sodium tungstate dihydrate (0.5 mmol) were dissolved to prepare a mixed reagent (pH 6.5). After 7.3 g of 2-ethyl-1,3-hexanediol (50.0 mmol) was dissolved into 100 mL of N,N-dimethylacetamide, the resultant was heated to 90° C., and the above mixed reagent was added. After the reaction was continued at 90° C. for four hours, 100 mL of toluene and 100 g of 10% brine were added for liquid separation. The aqueous layer was extracted three times with 100 mL of toluene, and all the organic layers were combined and concentrated under reduced pressure. The concentrated liquid was separated and purified by silica gel chromatography (developing solvent hexane:ethyl acetate=3:2) to obtain oily 2-ethyl-1-hydroxy-3-hexanone. The yield was 5.33 g (73%).

Example 7

[Chemical Formula 14]

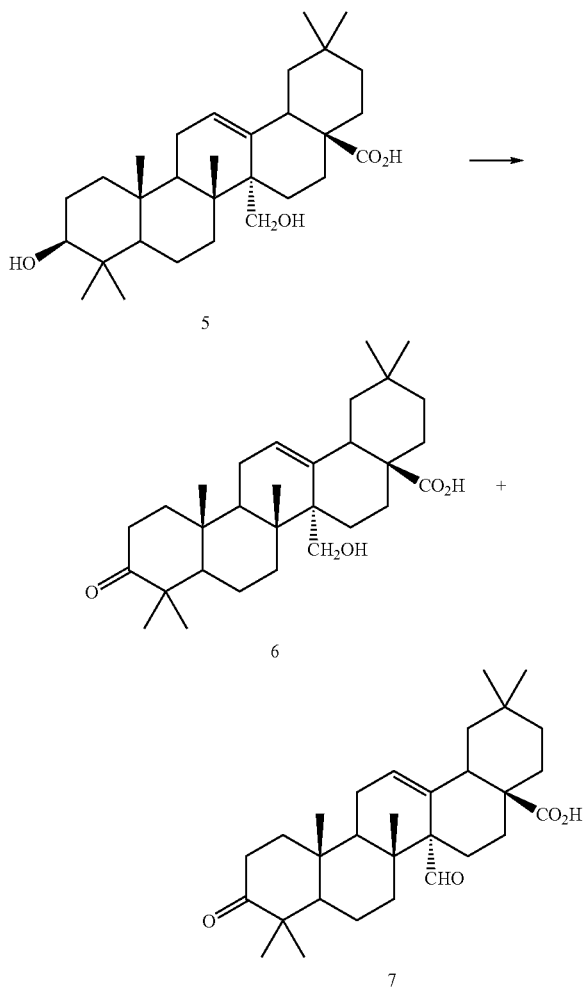

After 10.5 mg of sodium tungstate dihydrate (0.032 mmol) was dissolved into 100 mg of 35% hydrogen peroxide solution (1.016 mmol), phosphate buffer (4.49 mg of disodium phosphate dodecahydrate (0.012 mmol), 1.98 mg of monosodium phosphate dihydrate (0.013 mmol), and 257 mg of water) was added to prepare a mixed reagent. The compound 5 (300 mg, 0.635 mmol) was dissolved into 3.0 mL of DMA, and the mixture was heated to 90° C., followed by dropwise addition of the above mixed reagent. After the dropwise addition was completed, the reaction was continued at 90° C. for 6 hours.

The yield was calculated by quantitating the reaction liquid by HPLC. The yield of the compound 6 was 30%, and the yield of the compound 7 was 57%.

Example 8

After 10.5 mg of sodium tungstate dihydrate (0.032 mmol) was dissolved into 100 mg of 35% hydrogen peroxide solution (1.016 mmol), phosphate buffer (4.49 mg of disodium phosphate dodecahydrate (0.012 mmol), 1.98 mg of monosodium phosphate dihydrate (0.013 mmol), and 257 mg of water) was added to prepare a mixed reagent. The compound 5 (300 mg, 0.635 mmol) was dissolved into 3.0 mL of DMA, and the mixture was heated to 40° C., followed by dropwise addition of the above mixed reagent. After the dropwise addition was completed, the reaction was continued at 40(C for 23 hours.

The yield ratio was calculated by quantitating the reaction liquid by HPLC. The yield ratio of the compound 6 was 68%, and the yield ratio of the compound 7 was 18%.

Example 9

Into 4.34 g of 35% hydrogen peroxide solution (44.7 mmol), 95.76 mg of disodium phosphate dodecahydrate (0.3 mmol) and 101 mg of sodium tungstate dihydrate (0.4 mmol) were dissolved to prepare a mixed reagent (pH 6.3). After 1.00 g of cyclohexanol (10.0 mmol) was dissolved into 27 mL of N,N-dimethylacetamide, the resultant was heated to 90(C, and the above mixed reagent was added. The reaction was continued for ten hours to obtain cyclohexanone. The yield ratio was 96.2% (GC quantification).

The non-patent document 10 discloses that the Baeyer-Villiger reaction proceeds when 4.4 mol equivalent of hydrogen peroxide is used with respect to 1 mol of cyclohexanol. However, according to the process of the present invention, the above-mentioned reaction hardly proceeded, and ketone was obtained from a secondary alcohol in a good manner.

INDUSTRIAL APPLICABILITY

The oxidation process of an alcohol of the present invention is a process that is suitable for industrial production because of being safe and having a high applicability.

The invention claimed is:
1. A process of oxidizing an alcohol comprising:
 preparing a solution comprising the alcohol in an amide solvent; and
 reacting the alcohol with hydrogen peroxide and a tungsten catalyst.
2. A process of oxidizing alcohol comprising:
 preparing a solution comprising an alcohol in an amide solvent;
 obtaining a mixed reagent comprising hydrogen peroxide and water and a tungsten catalyst; and
 reacting the alcohol with the mixed reagent.
3. The process of claim 2, wherein the mixed reagent further comprises phosphoric acid or a salt thereof, or a hydrate thereof.
4. The process of claim 2 or 3, wherein the pH value of the mixed reagent or the pH value in the reaction system before the start of reaction is 2 or above.
5. The process of claim 2 or 3, wherein the pH value of the mixed reagent or the pH value in the reaction system before the start of reaction is 5 or above.
6. The process of any one of claims 2 or 3, wherein the pH value of the mixed reagent or the pH value in the reaction system before the start of reaction is 8 or below.
7. The process of claim 1, wherein the solution further comprises phosphoric acid or a salt thereof, or a hydrate thereof.
8. The process of claim 1 2, or 3, wherein the tungsten catalyst is tungstic acid or sodium tungstate, or a hydrate thereof.
9. The process of claim 1 2, or 3, wherein the amide solvent is N,N-dimethylacetamide.

10. The process of claim 3 or 7, wherein the phosphoric acid or a salt thereof, or a hydrate thereof is disodium phosphate, monosodium phosphate or a hydrate thereof, or a mixture thereof.

11. A process of producing a compound represented by the formula (II):

[Chemical Formula 2]

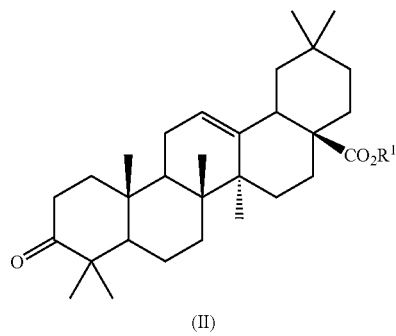

(II)

(wherein $R^1$ is hydrogen or lower alkyl)
characterized by oxidizing a compound represented by the formula (I):

[Chemical Formula 1]

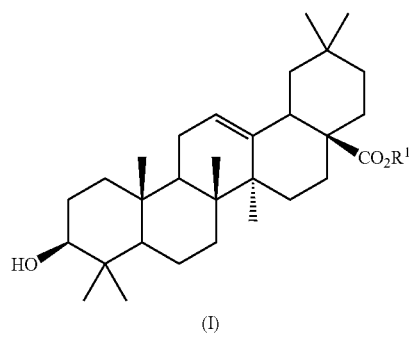

(I)

(wherein $R^1$ is hydrogen or lower alkyl)
in an amide solvent with use of hydrogen peroxide and a tungsten catalyst.

12. A process of producing a compound represented by the formula (III):

[Chemical Formula 3]

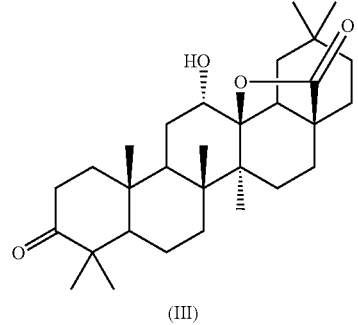

(III)

characterized in that the compound (II) obtained by the process of claim 11 is successively subjected to ozone oxidation without isolation.

* * * * *